(12) United States Patent
Seto et al.

(10) Patent No.: US 9,820,635 B2
(45) Date of Patent: Nov. 21, 2017

(54) BENDING TUBE FOR ENDOSCOPE AND ENDOSCOPE

(71) Applicant: OLYMPUS CORPORATION, Tokyo (JP)

(72) Inventors: Hideyuki Seto, Hino (JP); Eijiro Sato, Hachioji (JP); Takeru Kondo, Hachioji (JP); Takashi Nara, Musashino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/969,553

(22) Filed: Dec. 15, 2015

(65) Prior Publication Data

US 2016/0100745 A1 Apr. 14, 2016

Related U.S. Application Data

(63) Continuation of application No. PCT/JP2014/076086, filed on Sep. 30, 2014.

(30) Foreign Application Priority Data

Feb. 18, 2014 (JP) ................................ 2014-028933

(51) Int. Cl.
*A61B 1/005* (2006.01)
*A61B 17/00* (2006.01)
(Continued)

(52) U.S. Cl.
CPC ............ *A61B 1/0055* (2013.01); *G02B 23/24* (2013.01); *A61B 1/0057* (2013.01); *A61B 1/307* (2013.01);
(Continued)

(58) Field of Classification Search
CPC ................ A61B 1/0055; A61B 1/0056; A61B 2017/00309; A61M 25/0054; A61M 25/0138
See application file for complete search history.

(56) References Cited

U.S. PATENT DOCUMENTS

2007/0282358 A1 12/2007 Remiszewski et al.
2011/0112365 A1 5/2011 Galperin et al.
2014/0053940 A1* 2/2014 Konstorum ....... A61M 25/0138
138/118

FOREIGN PATENT DOCUMENTS

JP 2009-537280 A 10/2009
JP 2012-528651 A 11/2012
(Continued)

OTHER PUBLICATIONS

International Search Report dated Jan. 6, 2015 issued in PCT/JP2014/076086.

*Primary Examiner* — Timothy J Neal
*Assistant Examiner* — Aaron B Fairchild
(74) *Attorney, Agent, or Firm* — Scully, Scott, Murphy & Presser, P.C.

(57) ABSTRACT

In a bending tube for endoscope on which torsion preventing tab mechanisms are provided on the respective middle parts of first and second slots for bending located in an area from the proximal end of a bending tube body to a predetermined position on the distal end side (the torsion suppressing area), and the bending tube body being permitted to bend by the first and second slots for bending, the torsion preventing tab mechanism of at least any one of the first and second slots for bending arranged on the proximal end side of each of arrays (first and second arrays), other than the first and second slots for bending located at the most proximal end, among the first and second slots for bending arrayed in a
(Continued)

same line, respectively, along a longitudinal direction of the bending tube body, is removed.

7 Claims, 13 Drawing Sheets

(51) Int. Cl.
*G02B 23/24* (2006.01)
*A61B 1/307* (2006.01)
*A61M 25/00* (2006.01)
*A61M 25/01* (2006.01)

(52) U.S. Cl.
CPC .............. *A61B 2017/00309* (2013.01); *A61M 25/0054* (2013.01); *A61M 25/0138* (2013.01); *A61M 25/0147* (2013.01)

(56) References Cited

FOREIGN PATENT DOCUMENTS

| | | |
|---|---|---|
| JP | 2013-545553 A | 12/2013 |
| WO | WO 2007/136829 A1 | 11/2007 |
| WO | WO 2012/073072 A1 | 6/2012 |

\* cited by examiner

BENDING TUBE FOR ENDOSCOPE AND ENDOSCOPE

CROSS REFERENCE TO RELATED APPLICATION

This application is a continuation application of PCT/JP2014/076086 filed on Sep. 30, 2014 and claims benefit of Japanese Application No. 2014-028933 filed in Japan on Feb. 18, 2014, the entire contents of which are incorporated herein by this reference.

BACKGROUND OF INVENTION

1. Field of the Invention

The present invention relates to a bending tube for endoscope which performs a bending motion according to an operation of an operation portion and an endoscope.

2. Description of the Related Art

Conventionally, an endoscope which causes an object image of an inside of a body cavity to be displayed on a screen of a display device or the like by inserting an elongated insertion portion into the body cavity has been widely used. In general, a bending portion is provided on a distal end side of the insertion portion of the endoscope of this kind, and the bending portion is configured, for example, so that it freely bends in two directions of up and down, two directions of right and left or four directions of the up, down, right and left associated with the object image displayed on the display device or the like.

Recently, a bending tube for which a super-elastic alloy material is used has been proposed as a bending tube constituting such a bending portion. For the bending tube of this kind, for example, it is possible to realize a simple configuration without using a joint piece, a rotation pin or the like and easily realize diameter reduction, by providing a plurality of slots on a cylindrical-shaped pipe material (a bending tube body) using laser machining or the like.

Therefore, it is expected to adopt a bending tube made of a super-elastic alloy for an endoscope for which diameter reduction is especially required, such as a pyeloscope. In such an endoscope, it is common to adopt a configuration in which the bending portion can bend only in the two directions of up and down or only in the two directions of right and left in order to realize diameter reduction of the insertion portion more effectively. In the endoscope capable of bending only in two directions, it becomes possible to cause a distal end portion to be oriented to an arbitrary direction in a body cavity by combining a bending operation of the bending portion and a rotation-around-axis operation of the insertion portion.

In this case, for example, Japanese Patent Application Laid-Open Publication No. 2012-528651 (Patent Literature 1) discloses a technique in which each groove (each slot) arranged in a predetermined area which includes a proximal end side of a tube (a bending tube) is machined into a three-dimensionally bent zigzag shape (a crank shape) to form a projecting portion (a tab) and a pocket in the groove, and torsion of the bending tube is prevented by engaging the projection portion and the pocket, as a technique for preferably transmitting rotation torque around an axis given to the bending tube.

SUMMARY OF THE INVENTION

A bending tube for endoscope according to one aspect of the present invention is a bending tube for endoscope including: a cylindrical-shaped bending tube body made of a super-elastic alloy, a plurality of slots for bending arrayed for each setting interval along a longitudinal axis direction of the bending tube body, each of the plurality of slots for bending extending in a circumferential direction of the bending tube body, and torsion preventing tab mechanisms formed at middle parts of the respective slots for bending in an area from a proximal end of the bending tube body to a predetermined position on a distal end side, the bending tube body being permitted to bend by the slots for bending; wherein, among the respective slots for bending arrayed in a same line along the longitudinal direction of the bending tube body, at least any one of the slots for bending located on a proximal end side of the array, other than the slot for bending located at a most proximal end does not comprise the torsion preventing tab mechanism; the respective slots for bending include a first array along one bending direction of the bending tube body and a second array along another bending direction of the bending tube body; and the slots for bending not comprising the torsion preventing tab mechanism are different between the first array and the second array.

Further, an endoscope according to an aspect of the present invention comprises the bending tube for endoscope.

DETAILED DESCRIPTION OF THE PREFERRED EMBODIMENT(S)

Figure 1:
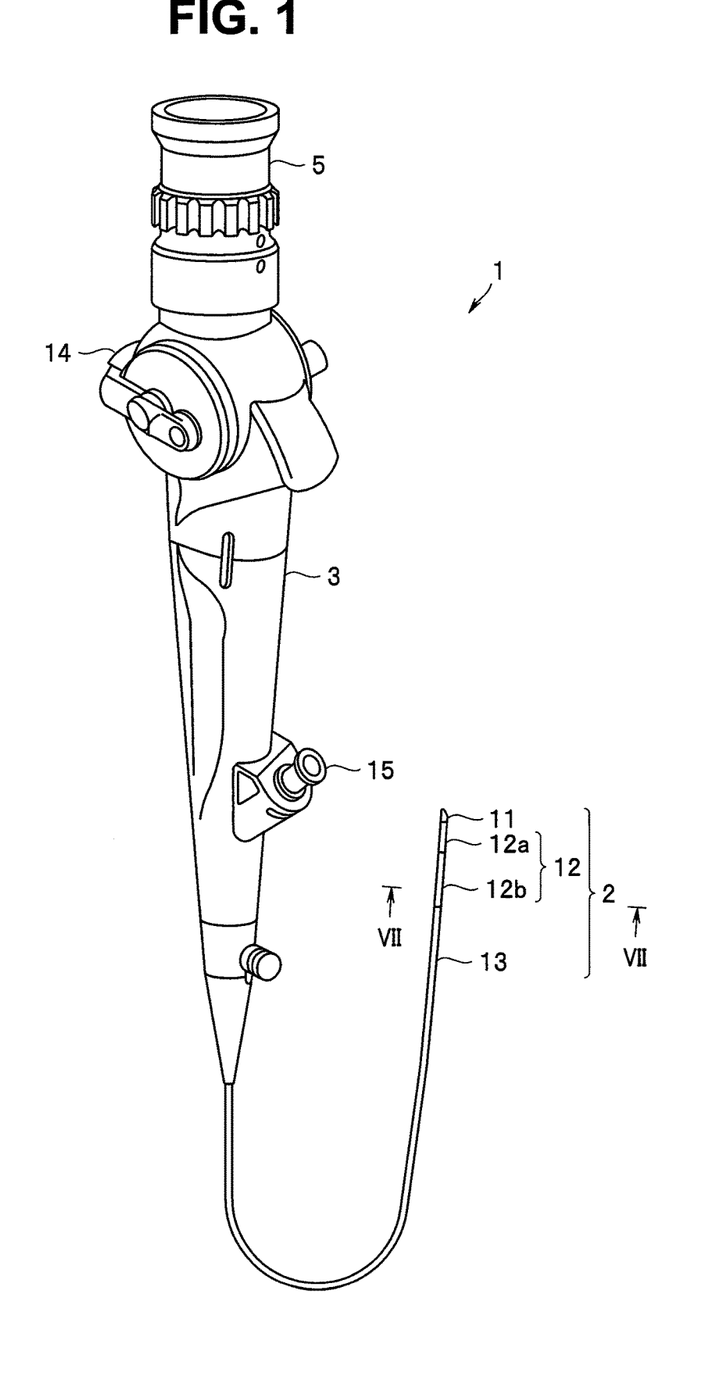
FIG. 1 is a perspective view of an endoscope.
Figure 2:
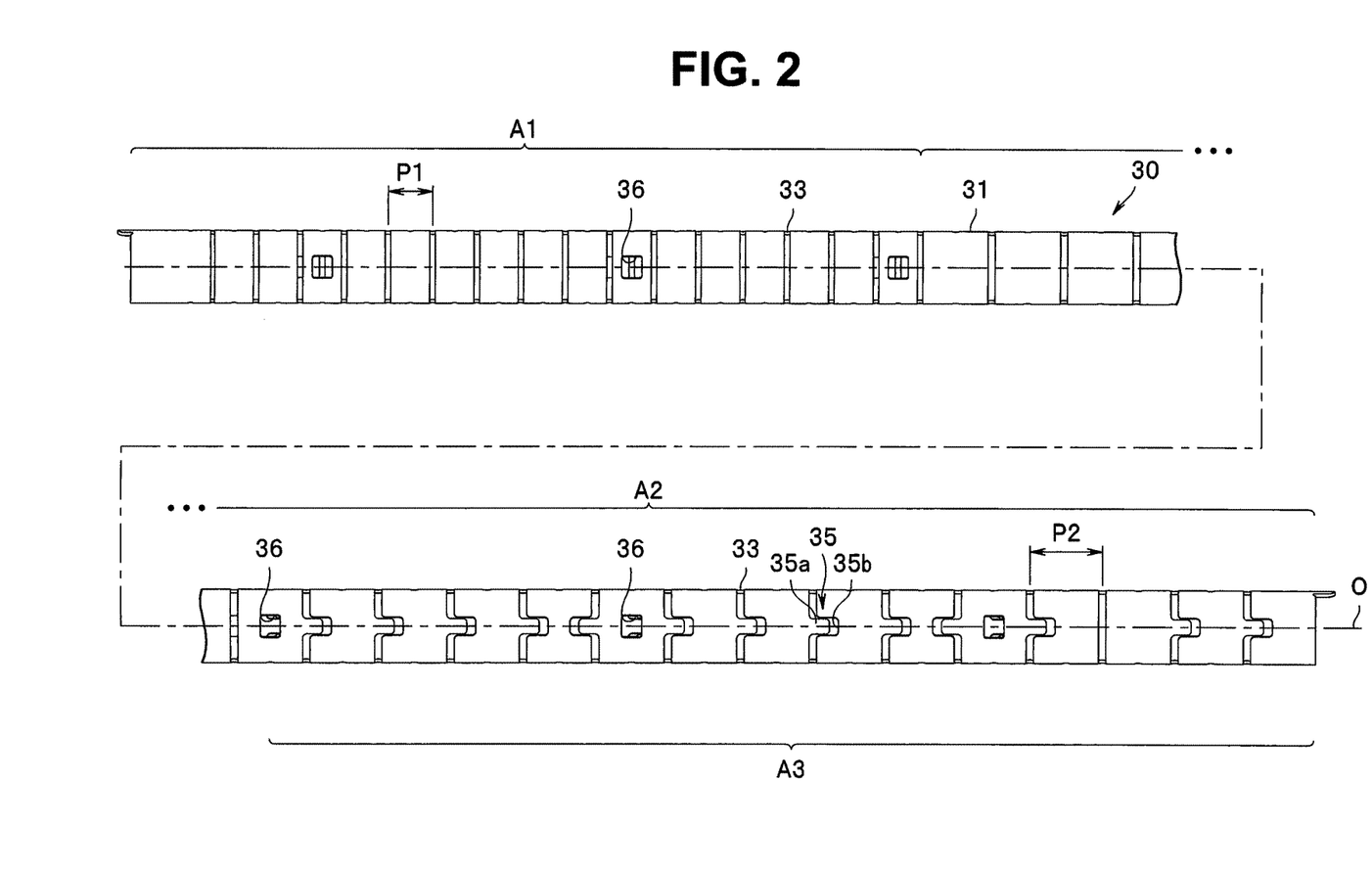
FIG. 2 is a top view of a bending tube.
Figure 3:
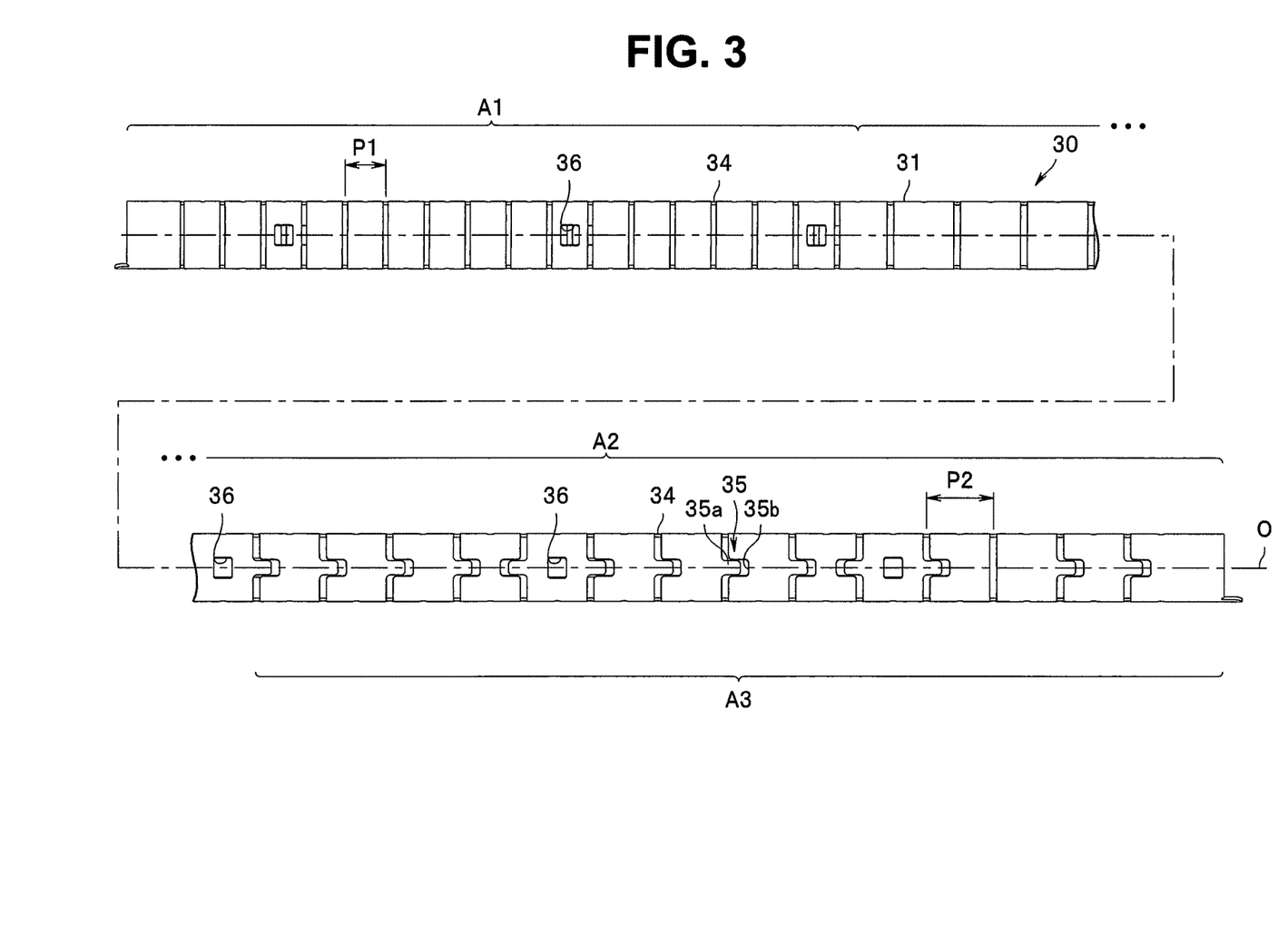
FIG. 3 is a bottom view of the bending tube.
Figure 4:
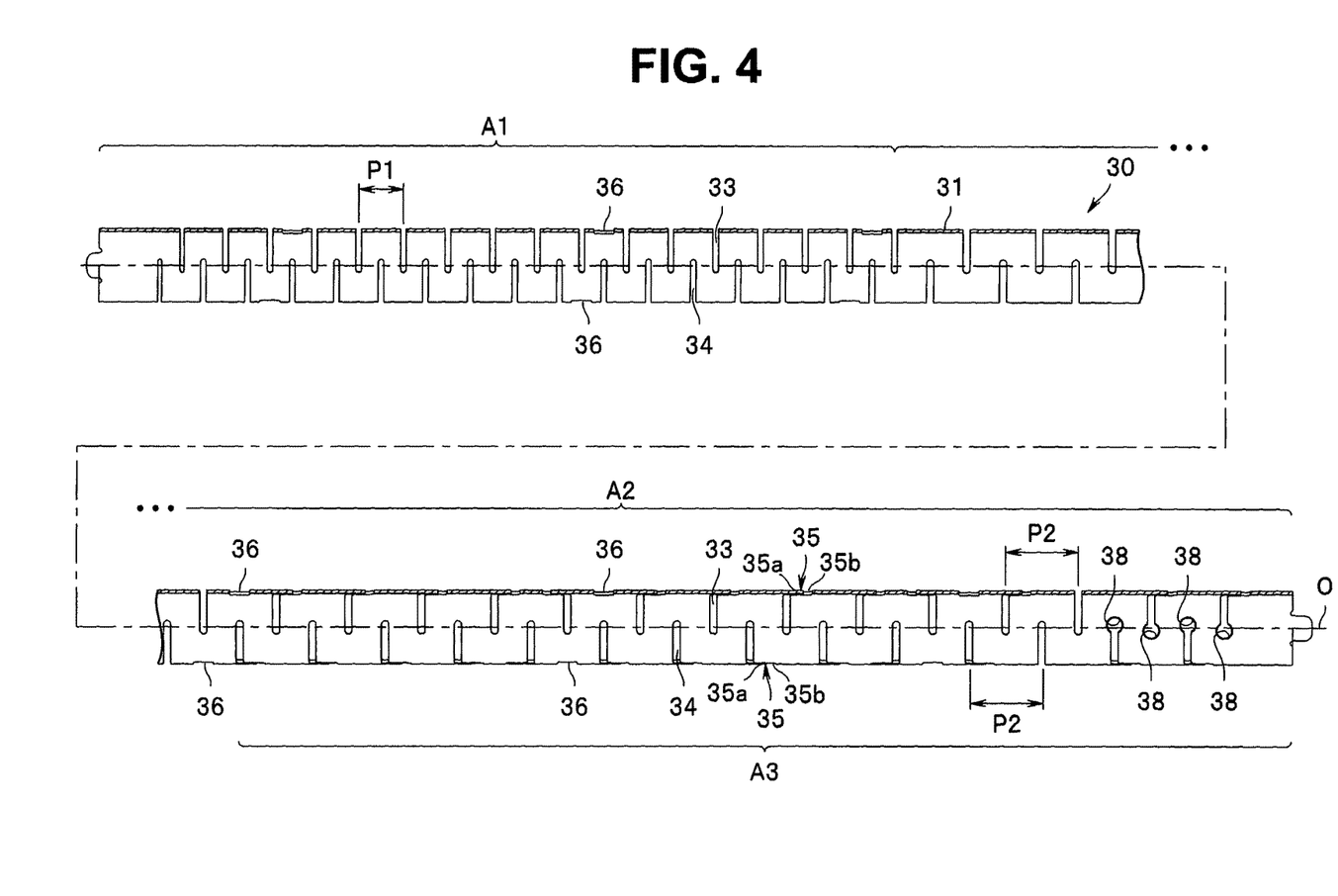
FIG. 4 is a left-cross-section side view showing a ruptured upper side of the bending tube.
Figure 5:
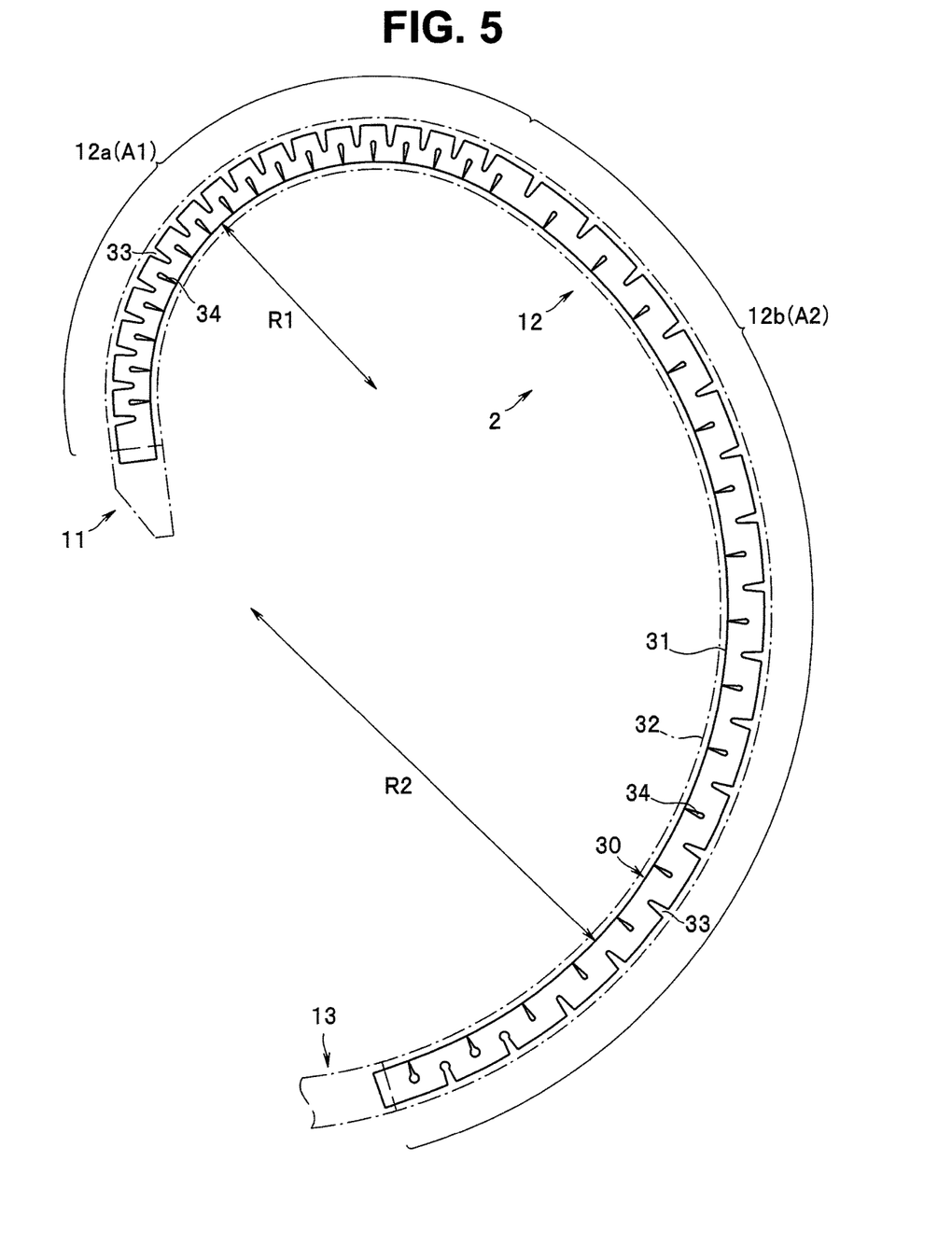
FIG. 5 is a right side view showing a state that the bending tube in a bending portion is bent upward.
Figure 6:
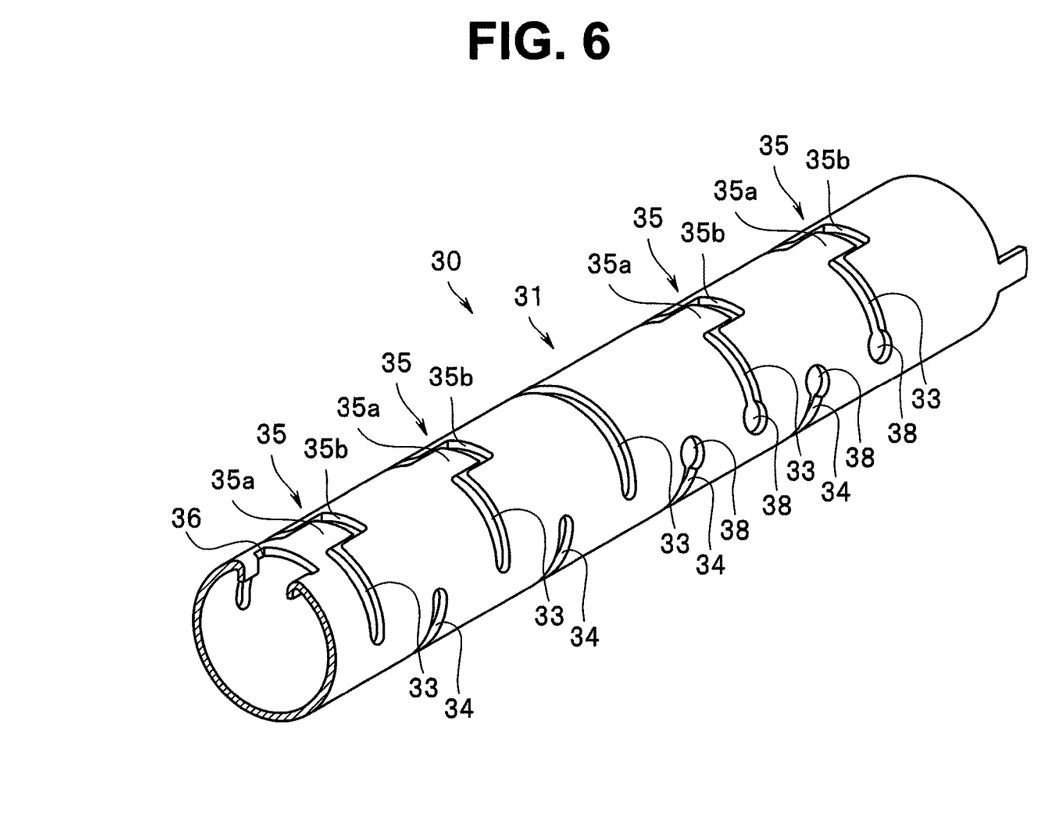
FIG. 6 is a perspective view showing a main part on a proximal end side of the bending tube.

An embodiment of the present invention will be described below with reference to drawings. The drawings relate to an embodiment of the present invention. FIG. 1 is a perspective view of an endoscope; FIG. 2 is a top view of a bending tube; FIG. 3 is a bottom view of the bending tube; FIG. 4 is a left-cross-section side view showing a ruptured upper side of the bending tube; FIG. 5 is a right side view showing a state that the bending tube is bent upward; and FIG. 6 is a perspective view showing a main part on a proximal end side of the bending tube.

An endoscope 1 shown in FIG. 1 is, for example, a pyeloscope, and the endoscope 1 is configured with a long insertion portion 2 to be inserted into a subject, an operation portion 3 provided at a proximal end of the insertion portion 2, and an eyepiece portion 5 provided at a proximal end of the operation portion 3. Here, in the present embodiment, the configuration of the endoscope 1 will be described with a configuration of a so-called fiberscope as an example. An endoscope to which the present invention is applied is, of course, not limited to a fiberscope.

The insertion portion 2 is configured having a distal end rigid portion 11 located on a distal end side, a bending portion 12 connectedly arranged at a proximal end of the distal end rigid portion 11, and a flexible tube portion 13 having flexibility which is connectedly arranged at a proximal end of the bending portion 12. Note that an observation lens, an illumination lens and the like not shown are provided in the distal end rigid portion 11.

Further, the bending portion 12 freely bends, for example, in two directions of up and down by a rotation operation of a bending lever 14 provided on the operation portion 3 being performed.

Figure 7:
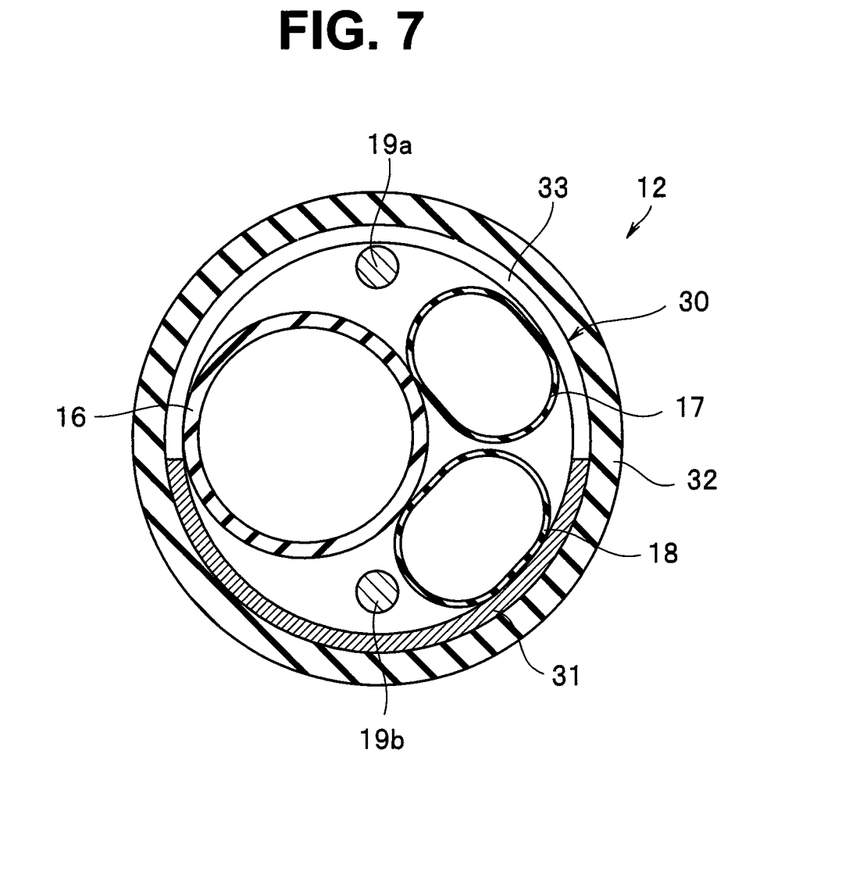
FIG. 7 is a cross sectional view along a VII-VII line in FIG. 1.

Further, the operation portion 3 is provided with a treatment instrument insertion opening 15. The treatment instrument insertion opening 15 leads to a proximal end side of a treatment instrument insertion channel 16 (see FIG. 7) inserted in the insertion portion 2. Thereby, a treatment instrument inserted into the treatment instrument insertion opening 15 can be led to the distal end side of the insertion portion 2 via the treatment instrument insertion channel 16 and can protrude into the subject from an opening formed on a distal end face of the distal end rigid portion 11.

Here, in addition to the treatment instrument insertion channel 16, a light guide 17 which transmits illuminating light to the illumination lens described above, an image guide 18 which transmits an optical image of an inside of the subject condensed on the observation lens described above to the eyepiece portion 5, angle wires 19a and 19b (see FIG. 7) for causing the bending portion 12 to perform a bending motion in linkage with a rotation operation of the bending lever 14, and the like are inserted in the insertion portion 2 and the operation portion 3.

Next, a configuration of the bending portion 12 will be described in detail. Note that, for example, as shown in FIGS. 1 and 5, the bending portion 12 is configured having a first bending portion 12a located on a distal end side and a second bending portion 12b connectedly arranged at a proximal end of the first bending portion 12a in the present embodiment. The first and second bending portions 12a and 12b are, for example, different in a minimum radius of curvature at time of bending, and a minimum radius of curvature R1 of the first bending portion 12a is set shorter than a minimum radius of curvature R2 of the second bending portion 12b (see FIG. 5). Note that the bending portion 12 is not limited to the configuration having two-stage minimum radiuses of curvature on the distal end side and the proximal end side. For example, a configuration in which the minimum radius of curvature is uniform from the distal end side to the proximal end side is, of course, possible.

As shown in FIGS. 2 to 7, the bending portion 12 is configured, for example, having a bending tube 30 mainly constituted by a cylindrical-shaped bending tube body 31 made of a super-elastic alloy material, and an outer cover 32 made of resin which covers a periphery of the bending tube 30. Here, as the super-elastic alloy material constituting the bending tube body 31, for example, Ni—Ti (nickel-titanium), titanium alloy, β titanium, pure titanium, 64 titanium, A7075 and the like are given. The super-elastic alloy is, however, not limited thereto.

The bending tube body 31 is provided with a plurality of slots for bending, for example, by laser machining, a basic shape of the slots for bending being a partial arc-shaped long hole which extends in a circumferential direction of the bending tube body 31.

For example, when specific description is made in the present embodiment in which the bending portion 12 freely bends in the two directions of up and down, the bending tube body 31 is provided with a plurality of first slots for bending 33 extending from an upside to a downside in a bending direction of the bending tube body 31 and a plurality of second slots for bending 34 extending from the downside to the upside in the bending direction of the bending tube body 31, as the slots for bending. Here, each slot for bending 33 and each slot for bending 34 are basically configured by such partial arc-shaped long holes forming mutually linearly symmetrical shapes relative to a longitudinal axis O.

As shown in FIGS. 2 to 4, the respective first slots for bending 33 are arrayed in line as a first array on one side in the circumferential direction of the bending tube body 31 (on the upside in the bending direction). The first slots for bending 33 are arranged in line for pitches P1 set in advance in a first bending area A1 set on the bending tube body 31, which corresponds to the first bending portion 12a, respectively, and are further arranged in line for pitches P2 (P1<P2) set in advance in a second bending area A2 set on the bending tube body 31, which corresponds to the second bending portion 12b, respectively.

Similarly, the respective second slots for bending 34 are arrayed in line as a second array on the other side in the circumferential direction of the bending tube body 31 (on the downside in the bending direction). The second slots for bending 34 are arrayed in line for the pitches P1 set in advance in the first bending area A1 set on the bending tube body 31, respectively, and are further arranged in line for the pitches P2 set in advance in the second bending area A2 set on the bending tube body 31, respectively.

Here, for example, as shown in FIG. 4, the second slots for bending 34 are arranged in the first bending area A1 in a state of being offset by half-pitch (P1/2) in the longitudinal axis O direction of the bending tube body 31, relative to the first slots for bending 33. Similarly, the second slots for bending 34 are arranged in the second bending area A2 in a state of being offset by half-pitch (P2/2) in the longitudinal axis O direction of the bending tube body 31, relative to the first slots for bending 33. By being offset in the longitudinal axis O direction, the respective first slots for bending 33 and the respective second slots for bending 34 are arranged on the bending tube body 31 without interfering with each other.

Furthermore, for example, as shown in FIGS. 2, 3 and 6, an area from a proximal end of the bending tube body 31 to a predetermined position on a distal end side (for example, a substantially central position of the bending tube body 31) is set as a torsion suppressing area A3 on the bending tube body 31. Basically, as for first and second slots for bending 33 and 34 arranged in the torsion suppressing area A3, a middle part is machined into a crank shape. Thereby, torsion preventing tab mechanisms 35 are formed at the middle parts of the first and second slots for bending 33 and 34. For example, as shown in FIGS. 2 and 3, the torsion preventing tab mechanism 35 is configured having a tab 35a arranged protruding in an axial direction of the bending tube body 31 and a pocket 35b recessedly arranged facing the tab 35a. When rotation torque around an axis acts on the bending tube body 31, torsion of the bending tube body 31 is prevented by the tab 35a and the pocket 35b being engaged with each other. Note that, in FIGS. 3 and 4, reference numeral 36 denotes a hole portion for attaching a wire guide, and the torsion preventing tab mechanism 35 at a part where the wire guide attaching hole portion 36 is formed is formed in a direction opposite to the direction of the torsion preventing tab mechanism 35 of other parts because of reasons of space.

For example, as shown in FIGS. 2 and 6, however, in the array of the first slots for bending 33, as for at least any one of first slots for bending 33 arranged on a proximal end side of the array, other than a first slot for bending 33 located at a most proximal end, the torsion preventing tab mechanism 35 is removed. Specifically, for example, among the first slots for bending 33 arrayed in the torsion suppressing area A3, a first slot for bending 33 at a third position from the most proximal end is formed without its middle part being machined into the crank shape, and the torsion preventing tab mechanism 35 of the first slot for bending 33 is omitted, in the present embodiment.

For example, as shown in FIG. 3, in the array of the second slots for bending 34, as for at least any one of second slots for bending 34 arranged on the proximal end side of the array, other than a second slot for bending 34 located at the most proximal end, the torsion preventing tab mechanism 35 is removed. Specifically, for example, among the second slots for bending 34 arrayed in the torsion suppressing area A3, a second slot for bending 34 at the third position from the most proximal end is formed without its middle part being machined into the crank shape, and the torsion preventing tab mechanism 35 of the second slot for bending 34 is omitted, in the present embodiment.

Here, it is because of a following reason that the torsion preventing tab mechanisms 35 of the first and second slots for bending 33 and 34 at the third position from the most proximal end are omitted in the first and second arrays shown in the present embodiment. That is, as a result of the inventor et al. performing, for example, simulation of giving rotation torque around the axis to the bending tube 30, it is revealed that stress by the rotation torque concentrates mainly on first and second slots for bending 33 and 34 located at the most proximal end and a second position, and, especially, concentration on the first and second slots for bending 33 and 34 located at the most proximal end is remarkable. It is also revealed that, in order to relieve (disperse) the concentration of stress, it is effective to permit torsion of the first and second slots for bending 33 and 34 located on the proximal end side, and, especially, it is effective to permit torsion of first and second slots for bending 33 and 34 located at the third and fourth positions from the most proximal end. Therefore, in the present embodiment, the torsion preventing tab mechanisms 35 of the first and second slots for bending 33 and 34 located at the third position are omitted in order to most effectively relieve the concentration of stress on the first and second slots for bending 33 and 34 at the most proximal end and the second position.

Further, in the present embodiment, in order to enhance durability against the concentration of stress on the first and second slots for bending 33 and 34 located at the most proximal end and the second position, circular holes 38 as stress concentration preventing portions are provided at end portions of these first and second slots for bending 33 and 34. A diameter of the circular holes 38 is set longer than a width of the first and second slots for bending 33 and 34, and, thereby, it is possible to disperse stress concentrated on end portions of the slots.

According to such an embodiment, on the bending tube for endoscope 30 on which the torsion preventing tab mechanisms 35 are provided on the respective middle parts of the first and second slots for bending 33 and 34 located in the area from the proximal end of the bending tube body 31 to a predetermined position on the distal end side (the torsion suppressing area A3), and the bending tube body 31 being permitted to bend by the first and second slots for bending 33 and 34, the torsion preventing tab mechanism 35 of at least any one of the first and second slots for bending 33 and 34 arranged on the proximal end side of each of the arrays (the first and second arrays), other than the first and second slots for bending 33 and 34 located at the most proximal end, among the first and second slots for bending 33 and 34 arrayed in a same line, respectively, along a longitudinal direction of the bending tube body 31, is removed. Thereby, it is possible to enhance the durability without decreasing torsional rigidity around the axis of the bending tube 30 more than necessary. Especially, though, in the endoscope 1 according to the embodiment provided with the bending portion 12 which permits bending only in two directions, a bending operation of the bending portion 12 and a rotation-around-axis operation of the insertion portion 2 are combined in order to orient the distal end rigid portion 11 to an arbitrary direction in a body cavity. However, it is possible to enhance the durability of the bending tube 30 while maintaining the torsional rigidity around the axis which appropriately copes with such a rotation operation.

In this case, by omitting only the torsion preventing tab mechanisms 35 of the first and second slots for bending 33 and 34 at the third position located nearest to the first and second slots for bending 33 and 34 at the most proximal end and the second position, on which concentration of stress is especially remarkable, it is possible to effectively enhance the durability without significantly decreasing the torsional rigidity around the axis of the bending tube 30 as a whole.

By providing the circular hole 38 at the end portions of the first and second slots for bending 33 and 34 located at the most proximal end and the second position, it is possible to more effectively enhance the durability against the rotation torque around the axis.

Figure 8:
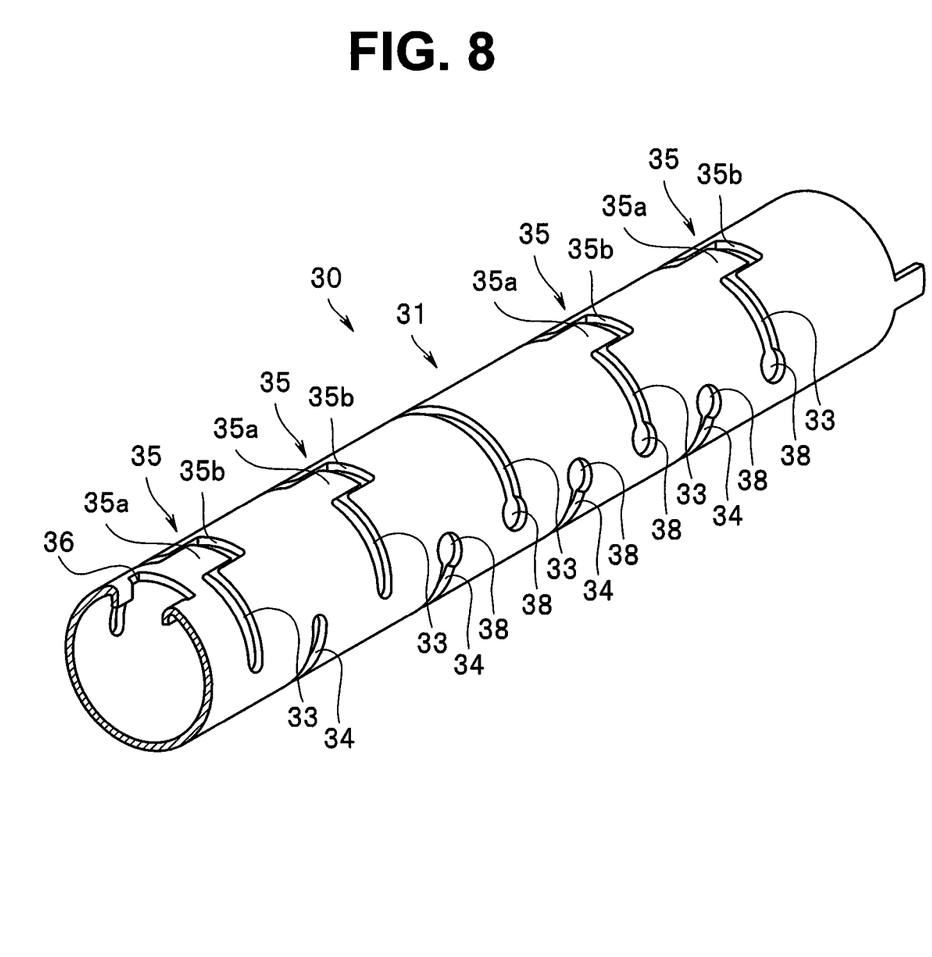
FIG. 8 is a perspective view relating to a first modification and showing a main part on the proximal end side of the bending tube.

Here, though an example has been described in the embodiment described above in which the circular holes 38 are formed only at the end portions of the first and second slots for bending 33 and 34 located at the most proximal end and the second position, it is also possible to provide the circular holes 38 for the end portions of the first and second slots for bending 33 and 34 at the third position where increase in stress is expected because of removal of the torsion preventing tab mechanisms 35, for example, as shown in FIG. 8.

Figure 9:
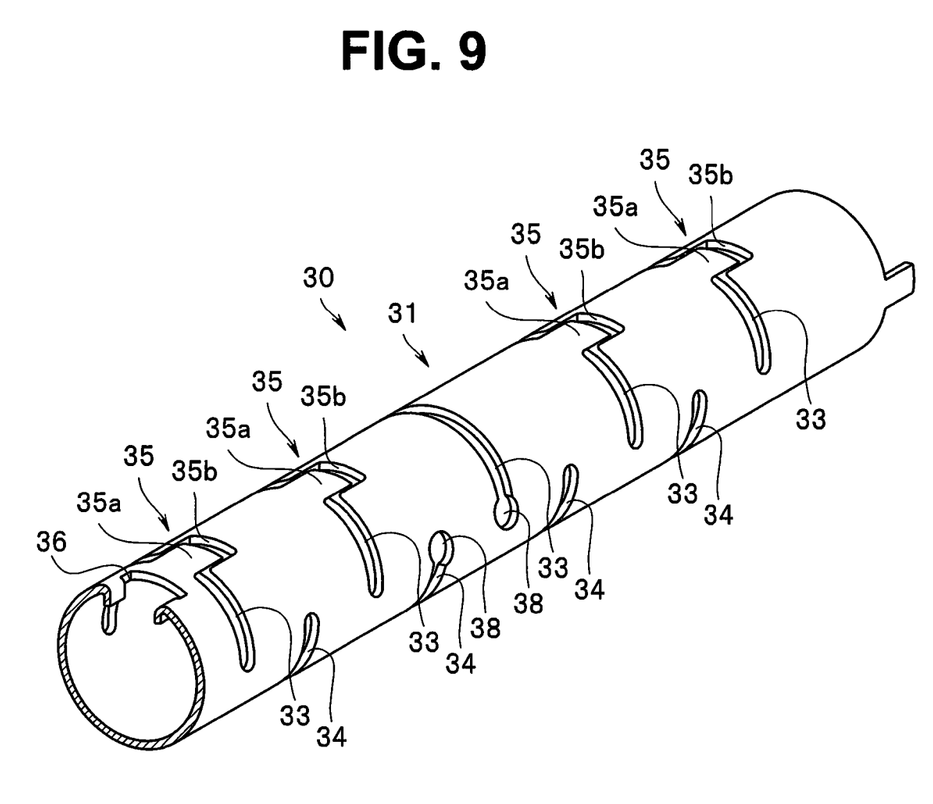
FIG. 9 is a perspective view relating to a second modification and showing the main part on the proximal end side of the bending tube.

On the contrary, it is also possible to provide the circular holes 38 only for the first and second slots for bending 33 and 34 at the third position on which increase in stress due to removal of the torsion preventing tab mechanisms 35 is expected, for example, as shown in FIG. 9.

Figure 10:
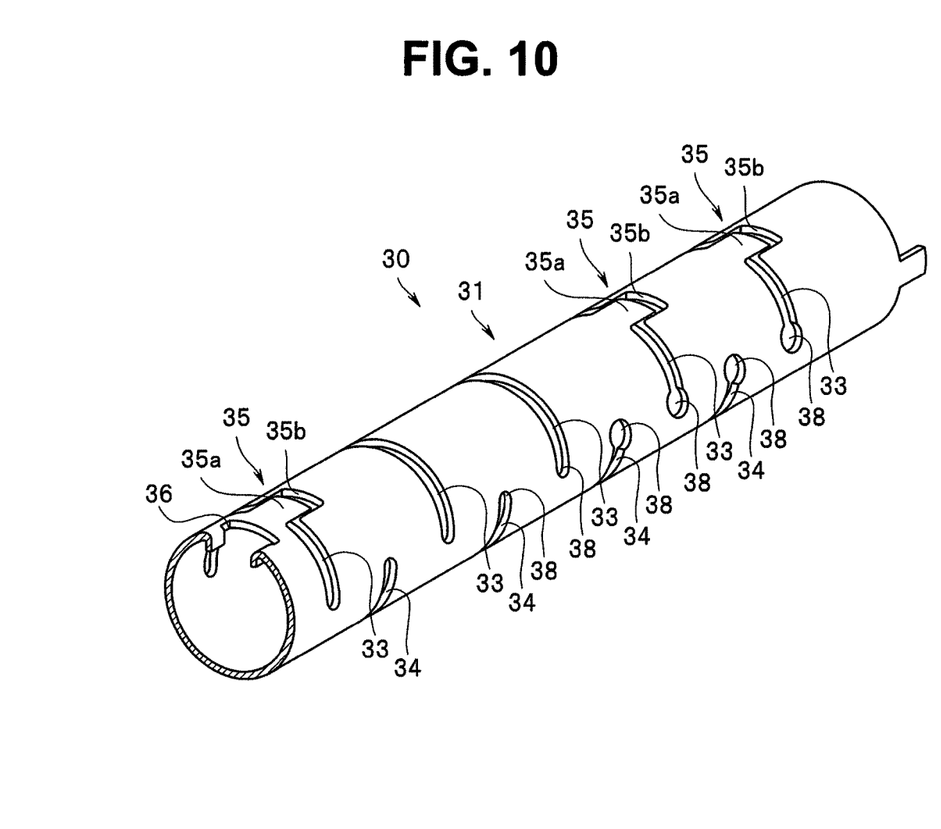
FIG. 10 is a perspective view relating to a third modification and showing the main part on the proximal end side of the bending tube.

Further, though description has been made on an example of removing the torsion preventing tab mechanisms 35 only from the first and second slots for bending 33 and 34 located at the third position, among the first and second slots for bending 33 and 34 on the torsion suppressing area A3 in the embodiment described above, it is also possible to, for example, as shown in FIG. 10, remove the torsion preventing tab mechanisms 35 from the first and second slots for bending 33 and 34 at the fourth position from the most proximal end also, depending on rigidity required from the torsion suppressing area A3, the pitch of each slot, or the like.

Figure 11:
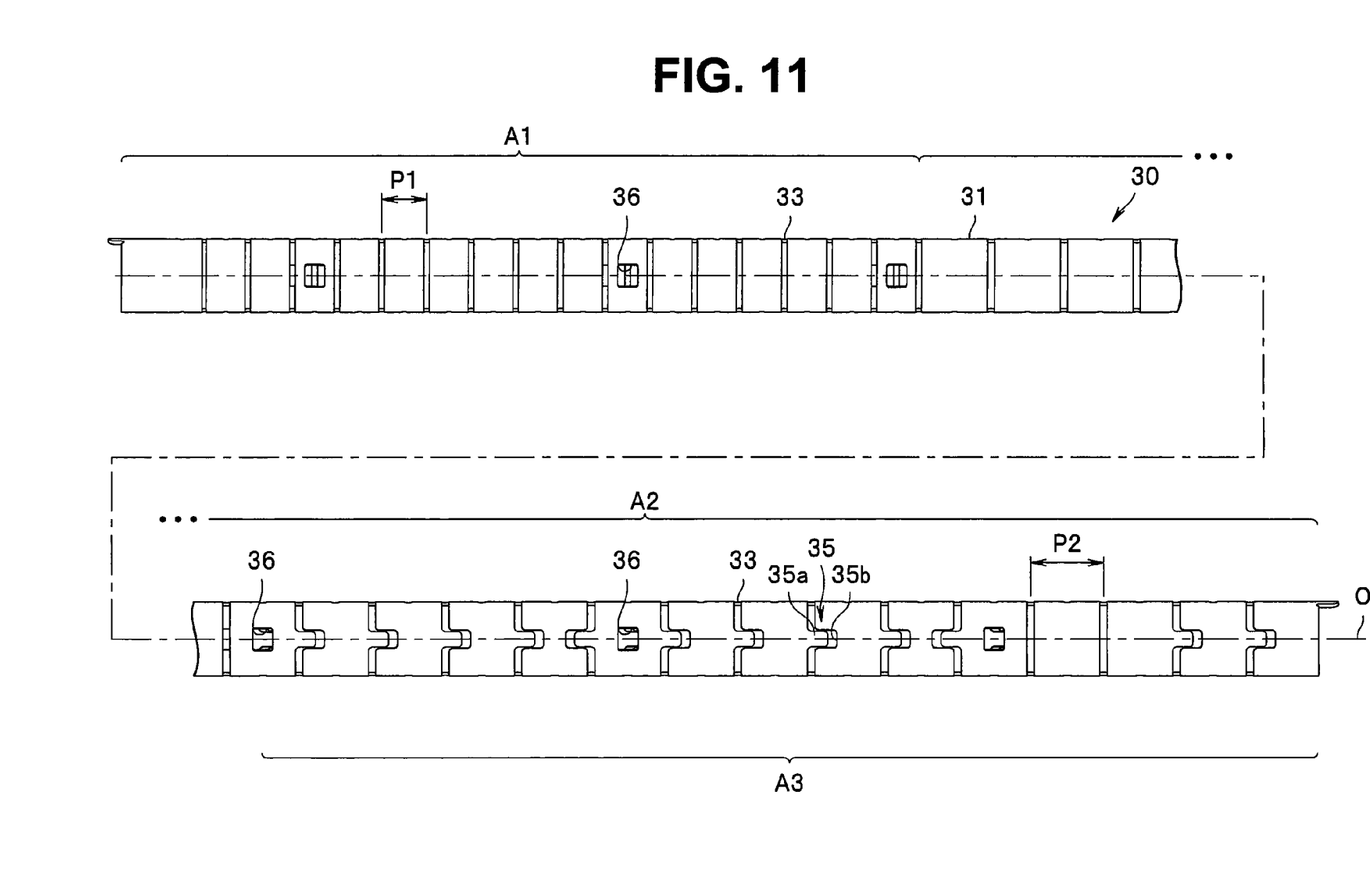
FIG. 11 is a top view of the bending tube relating to a fourth modification.
Figure 12:
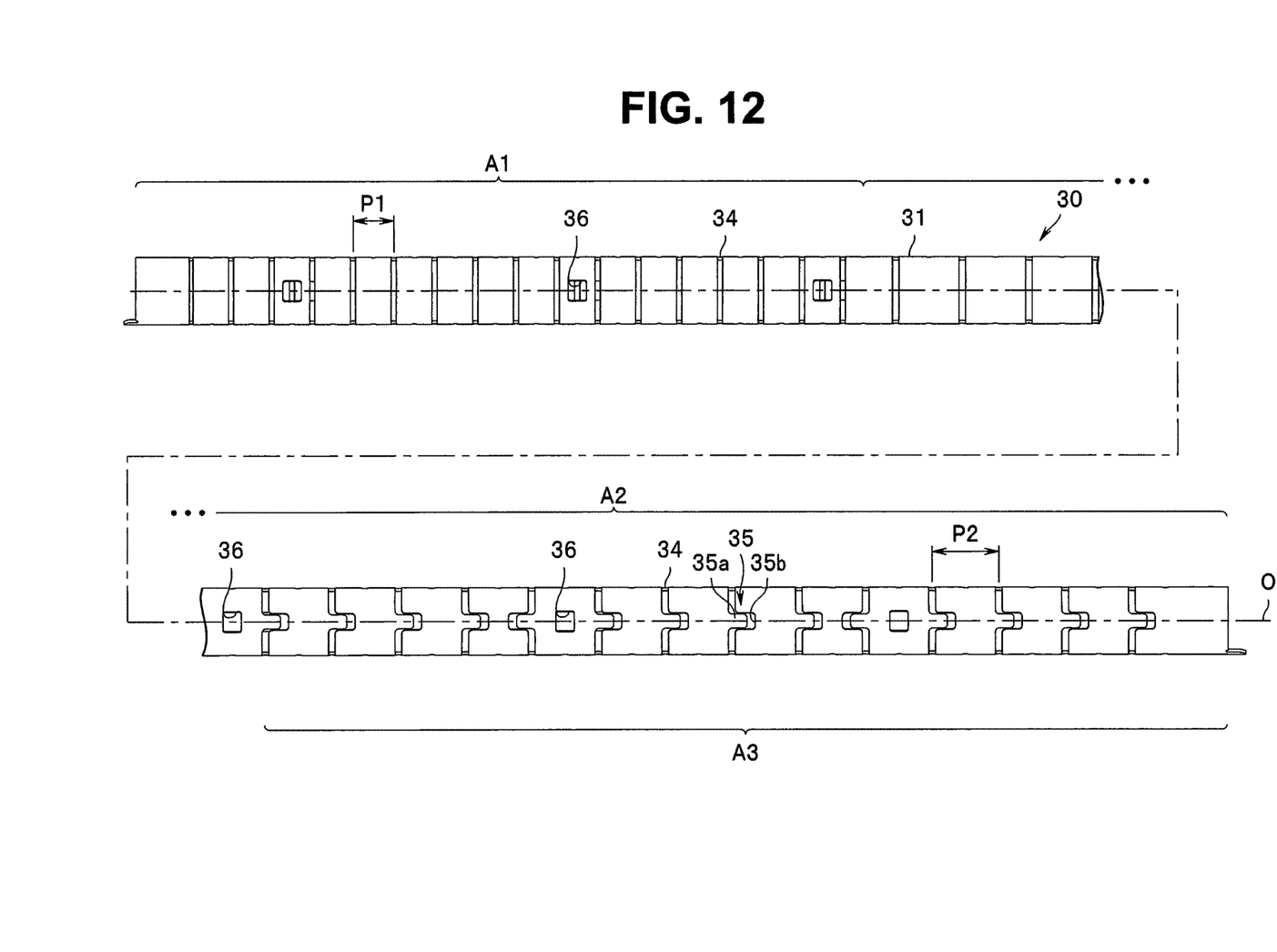
FIG. 12 is a bottom view of the bending tube relating to the fourth modification.

Further, though description has been made on an example of setting, for the first and second arrays, first and second slots for bending 33 and 34 corresponding to each other (for example, the first and second slots for bending 33 and 34 at the third position) as targets from which the torsion preventing tab mechanisms 35 are to be removed in the embodiment described above, it is also possible to cause the targets from which the torsion preventing tab mechanisms 35 are to be removed to be different from each other between the first and second arrays. For example, in examples shown in FIGS. 11 and 12, a configuration is shown in which torsion preventing tab mechanisms 35 at the third and fourth positions are removed for the first array, and, for the second array, no torsion preventing tab mechanisms 35 are removed. By adopting such a configuration, it is possible to, even when rigidities in respective bending directions differ from one another due to influence of what is inserted in the bending tube 30 and the like, enhance the durability while appropriately securing the torsional rigidity around the axis.

Figure 13:
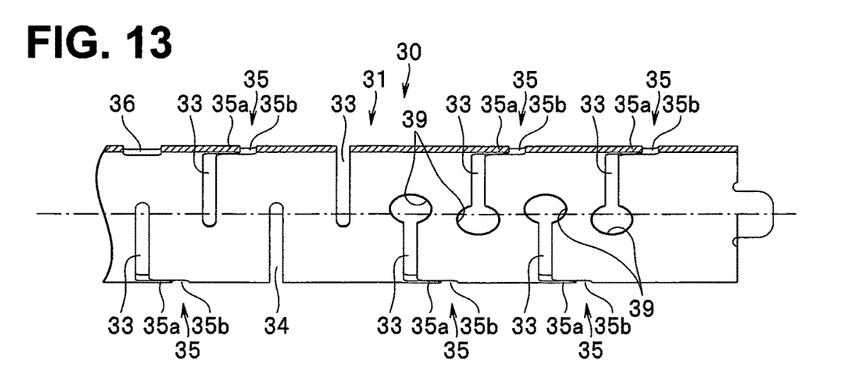
FIG. 13 is a left-cross-section side view relating to a fifth modification and showing the proximal end side of the bending tube, with an upper side ruptured.

Further, though description has been made on an example in which the stress concentration preventing portion is configured by the circular hole 38 in the embodiment described above, it is also possible to, for example, as shown in FIG. 13, configure the stress concentration preventing portion with such an elliptical hole 39 in which a longer side extends along a central axis of the bending tube body 31. In this case, it is desirable that the longer side of each elliptical hole 39 is set longer than the respective widths of the first and second slots for bending 33 and 34.

Figure 14:
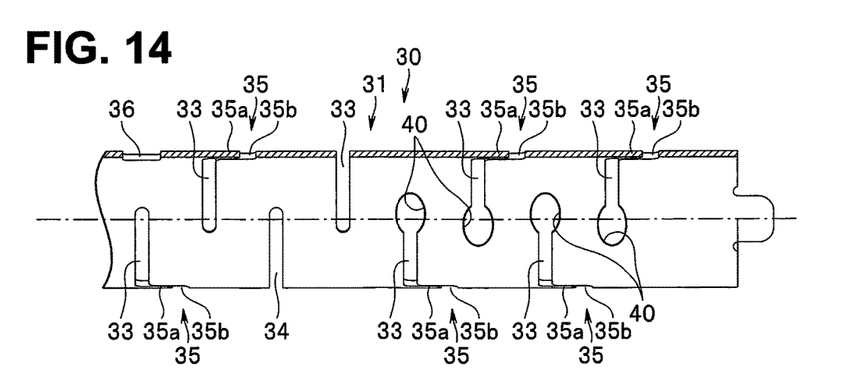
FIG. 14 is a left-cross-section side view relating to a sixth modification and showing the proximal end side of the bending tube, with the upper side ruptured.

Alternatively, it is also possible to, for example, as shown in FIG. 14, configure the stress concentration preventing portion with such an elliptical hole 40 in which a shorter side extends along the central axis of the bending tube body. In this case, it is desirable that the shorter side of each elliptical hole 40 is set longer than the respective widths of the first and second slots for bending 33 and 34.

Figure 15:
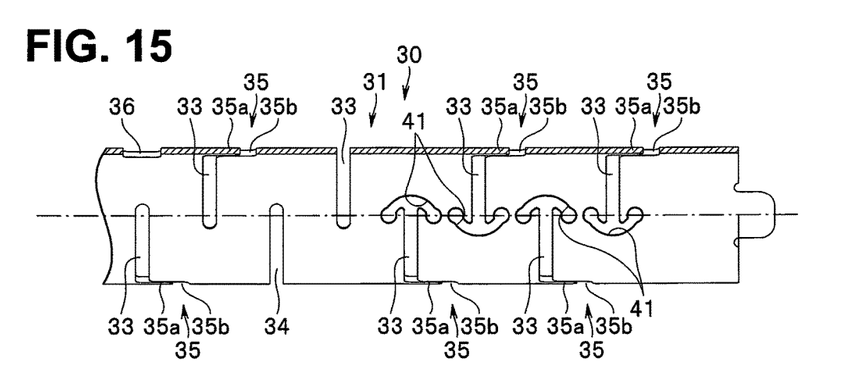
FIG. 15 is a left-cross-section side view relating to a seventh modification and showing the proximal end side of the bending tube, with the upper side ruptured.

Alternatively, it is also possible to, for example, as shown in FIG. 15, configure the stress concentration preventing portion by a hole portion 41 constituted by a combination of a plurality of circular arcs or the like. In this case, it is desirable that a width of each elliptical hole 41 is set wider than the respective widths of the first and second slots for bending 33 and 34.

Note that the present invention is not limited to each embodiment described above, and various modifications and changes are possible. The various modifications and changes are also within a technical scope of the present invention. Further, for example, it is, of course, possible to appropriately combine configurations of the embodiment and respective variations described above.

What is claimed is:

1. A bending tube for an endoscope, the bending tube comprising:
    a cylindrical-shaped bending tube body made of a super-elastic alloy, the bending tube body having:
        a first plurality of slots arrayed along a longitudinal axis direction of the bending tube body, each of the first plurality of slots extending in a circumferential direction of the bending tube body;
        a second plurality of slots arrayed along the longitudinal axis direction, each of the second plurality of slots extending in the circumferential direction of the bending tube body, the second plurality of slots being offset circumferentially from the first plurality of slots;
        a first torsion preventing tab mechanism extending from each individual slot of the first plurality of slots except for one or more of the first plurality of slots between a distal most slot of the first plurality of slots and a proximal most slot of the first plurality of slots; and
        a second torsion preventing tab mechanism extending from each individual slot of the second plurality of slots except for one or more of the second plurality of slots between a distal most slot of the second plurality of slots and a proximal most slot of the second plurality of slots;
    wherein a longitudinal position of the one or more of the first plurality of slots not having the torsion preventing tab mechanism is different from a longitudinal position of the one or more of the second plurality of slots not having the torsion preventing tab mechanism.

2. The bending tube for endoscope according to claim 1, wherein, in at least one of the first plurality of slots and the second plurality of slots, a slot at a third position from the proximal most slot does not comprise the torsion preventing tab mechanism.

3. The bending tube for endoscope according to claim 1, wherein the bending tube body further comprises a stress concentration preventing portion provided at an end portion of one or more of the first and second plurality of slots.

4. The bending tube for endoscope according to claim 3, wherein the stress concentration preventing portion is a circular hole with a diameter larger than a width of a respective one or more first and second plurality of slots.

5. The bending tube for endoscope according to claim 1, wherein the bending tube body further comprises a stress concentration preventing portion provided at an end portion of the one or more of the first and second plurality of slots not comprising the torsion preventing tab mechanism.

6. The bending tube for endoscope according to claim 5, wherein the stress concentration preventing portion is a hole portion with a wider width than the width of a respective one or more first and second plurality of slots.

7. An endoscope comprising the bending tube for endoscope according to claim 1.

* * * * *